(12) United States Patent
Shin

(10) Patent No.: US 11,173,225 B2
(45) Date of Patent: Nov. 16, 2021

(54) ANION ESSENTIAL-OIL FRAGRANCE MACHINE VIBRATION-WAVE-CONDUCTION CUP-BOTTOM-ELEMENT REINFORCEMENT AND REPLACEABLE WATER-CUP AND NOZZLE STRUCTURE

(71) Applicant: Fu-Zong Shin, Taipei (TW)

(72) Inventor: Fu-Zong Shin, Taipei (TW)

( * ) Notice: Subject to any disclaimer, the term of this patent is extended or adjusted under 35 U.S.C. 154(b) by 202 days.

(21) Appl. No.: 16/554,517

(22) Filed: Aug. 28, 2019

(65) Prior Publication Data
US 2021/0060200 A1    Mar. 4, 2021

(51) Int. Cl.
| | | |
|---|---|---|
| A61L 9/22 | (2006.01) | |
| A61L 9/12 | (2006.01) | |
| A61L 9/14 | (2006.01) | |
| A61L 9/013 | (2006.01) | |

(52) U.S. Cl.
CPC ............... *A61L 9/22* (2013.01); *A61L 9/122* (2013.01); *A61L 9/14* (2013.01); *A61L 9/013* (2013.01); *A61L 2209/12* (2013.01); *A61L 2209/132* (2013.01); *A61L 2209/133* (2013.01); *A61L 2209/134* (2013.01)

(58) Field of Classification Search
CPC ... A61L 9/122; A61L 9/14; A61L 9/22; A61L 2209/132; A61L 2209/133; A61L 2209/134
See application file for complete search history.

(56) References Cited

U.S. PATENT DOCUMENTS

2018/0326174 A1*  11/2018  Shin ................... B05B 17/0615

\* cited by examiner

*Primary Examiner* — Timothy C Cleveland
(74) *Attorney, Agent, or Firm* — Leong C. Lei

(57) ABSTRACT

An anion essential-oil fragrance machine vibration-wave-conduction cup-bottom-element reinforcement and replaceable water-cup and nozzle structure; especially an anion essential-oil fragrance machine which can prevent the heat-ablation crack of the bottom of the vibration-wave-conduction cup, which is generated by the long-term action of the high-temperature and high-speed-vibration frequency of the oscillation unit. Therefore, it can improve the conduction efficiency, prevent leakage, prolong the life of the machine-body components, improve the stability of the machine-body quality, reduce the non-performing rate and the burden of after-sales maintenance man-hours, and save time and effort.

4 Claims, 18 Drawing Sheets

ANION ESSENTIAL-OIL FRAGRANCE MACHINE VIBRATION-WAVE-CONDUCTION CUP-BOTTOM-ELEMENT REINFORCEMENT AND REPLACEABLE WATER-CUP AND NOZZLE STRUCTURE

(a) TECHNICAL FIELD OF THE INVENTION

An anion essential-oil fragrance machine vibration-wave-conduction cup-bottom-element reinforcement and replaceable water-cup and nozzle structure; especially an anion essential-oil fragrance machine which can prevent the heat-ablation crack of the bottom of the vibration-wave-conduction cup, which is generated by the long-term action of the high-temperature and high-speed-vibration frequency of the oscillation unit. Therefore, it can improve the conduction efficiency, prevent leakage, prolong the life of the machine-body components, improve the stability of the machine-body quality, reduce the non-performing rate and the burden of after-sales maintenance man-hours, and save time and effort.

(b) DESCRIPTION OF THE PRIOR ART

Aromatherapy has been discussed for a long time, and many media reports (such as Reader's Digest) have reported its evolution and application. However, in the cases cited in these reports, although there is still a reservation about whether aromatherapy can replace formal medical treatment, a lot of the given positive comments are still much optimistic.

Moreover, no matter it can really produce a universal healing effect on the human body or not, as long as the appropriate essential oil is used in the indoor environment to float out fragrance, it can naturally create a pleasant atmosphere and even a mind-soothing environment. As long as people's minds are stable, they will alleviate the feeling of discomfort, and they can easily handle things and improve EQ for emotional management. It can be said that there are many benefits. Conventionally, measures for dispersing essential oils in the air include a heating method (Burning candle/Plug-electricity type), an isopropanol aromatherapy method, and a micro-oxygen aromatherapy method. Because these methods generally have various factors such as the danger of heating and burning, the excessive generation of flagrant molecules or the adverse environment for ozone generation, experts do not recommend to use.

Recently, using the electric power to generate the vibration frequency has been applied; the supersonic aroma method of rapidly oscillating and finely atomizing to float out the mixed liquid of the mixed oil into the essential oil is the best method for accelerating refinement the essential oil without heating hazard. However, the ultrasonic aroma machine made by the ultrasonic aroma method cannot be said to have achieved perfection.

Please refer to FIG. 1A and FIG. 1B, which are respectively the schematic diagrams of the appearance and side structure of the conventional ultrasonic aroma machine. As can be seen from the figures, the ultrasonic aroma machine comprises a case 30, a gas-gathering unit 20, a nozzle 10, and an electronic-control assembly 40; wherein:

The case 30 is internally set with a vibration-wave-conduction cup 301 which an essential-oil-water cup 304 is set therein; and an oscillator chamber 30' which can be exactly embedded in the oscillator 302a is set below the vibration-wave-conduction cup 301. An oscillation unit 302 comprises an oscillator 302a and a heat-dissipation circuit-board 302b, wherein an induction rod 302b' is protrudedly set on the heat dissipation circuit board 302b; wherein the oscillation unit 302 is set under the vibration-wave-conduction cup 301 in a screw-connection manner, and a fan 303 is set under the oscillation unit 302. Thereby, the water is first placed in the vibration-wave-conduction cup 301, and the height needs to be higher than the induction rod 302b', and then the eight-point full essential-oil-water cup 304 is placed in; the electronic-control assembly 40 is activated and the oscillation unit 302 is acted to generate a high-frequency oscillation to instantaneously atomize the oil-water in the essential-oil-water cup 304. And, through the blast action of the fan 303, the refined essential oil water molecules are lifted up via the gas-gathering unit 20, and are ejected by the nozzle 10; thereby achieving the flagrance and replenishing the indoor air humidity, and it is favored by the market.

Please refer to FIG. 2A and FIG. 2B, which are respectively the oblique view and bottom view of a conventional vibration-wave-conduction cup and an oscillation unit. As is more clearly seen in the figures, there is an oscillator chamber 30' below the vibration-wave-conduction cup 301 which can be exactly embedded in the oscillator 302a. The oscillator 302a is embedded in an oscillation element 302a2 through a silicone seat 302a1, wherein an oscillation unit 302 comprises an oscillator 302a and a heat-dissipation circuit-board 302b, which are set under the vibration-wave-conduction cup 301 in a screw-connection manner.

However, the related products of the above-mentioned conventional inventions, through continuous testing and research by the inventor of the present invention, it is found that there are still some shortcomings, among which, please refer to the FIG. 2C and FIG. 2D, which are respectively the appearance schematic diagrams of the different angles of view of the conventional vibration-wave-conduction cup at the bottom. It can be clearly seen from the figures that when the above-mentioned ultrasonic aroma machine is acting, the oscillation unit generates a high frequency (2.4 million times per second) oscillation due to the long-term use; and the generated temperature and vibration frequency cause the heat-ablation crack 30" phenomenon of the bottom of the vibration-wave-conduction cup 301; which is easy to cause malfunction and leakage phenomenon of the machine parts, and also causes great troubles for after-sales service.

In view of the above-mentioned using shortcomings, the inventor has researched and improved to apply an approved patent; please refer to FIG. 3A and FIG. 3B, which are respectively the stereoscopic exploded diagram and side combination diagram of the bottom of the vibration-wave-conduction cup of the conventional anion essential-oil fragrance machine for the prevention structure of the ablation and crack. As can be clearly seen from the figures, the improved structure is opened and set with a through hole 401' at the bottom of the vibration-wave-conduction cup 401; wherein a silicone ring-sheet 406, an oscillator metal punch-seat 405, and an oscillation unit 402 are respectively set downward; wherein the silicone ring-sheet 406 is set with screw-column positioning notches on both sides, and the top surface is set with an annular sheet-like body of the inner-outer water-stop-protrusion; wherein the oscillator metal punch-seat 405 is a cap-body which is set with screw-column positioning notches on both sides and the top surface is set with a through hole; and, the oscillation unit 402 comprises an oscillator 404 and a heat-dissipation circuit-board 403; wherein the oscillator 404 is formed by embedding a oscillation element 4042 in a silicone seat 4041; wherein an annular water-stop-protrusion 4041' is set above the silicone seat 4041.

Please refer to the side combination diagram again, it can be clearly seen from this figure, when the oscillator 404 is assembled and screwed, the oscillator 4042 is first embedded in the silicone seat 4041, and then is jointly embedded into the oscillator metal punch-seat 405; wherein a plurality of screws 407 are used to respectively and from bottom to top to screw and combine the heat-dissipation circuit-board 403, the oscillator 404, the oscillator metal punch-seat 405, and the silicone ring-sheet 406 in the through hole 401' of the bottom of the vibration-wave-conduction cup 401; thereby exhibiting a tight fit. In this way, a tight fit can be formed to effectively reduce lateral vibration generation, and the high temperature and high-speed vibration frequency generated by the oscillation unit 402 due to long-term action can be prevented from causing heat-ablation crack phenomenon on the bottom of the vibration-wave-conduction cup 401; and the oscillator metal punch-seat 405 also effectively enhances durability.

However, when the above-mentioned components are used together, since the oscillation element 4042 is continuously vibrating for a long time, although it is not a sudden force, after a long time of use and actual operation, it still generates ablative damage to the machine parts; except for the heating deformation of the cup bottom, the small cracks are also unavoidable; and it is easy to cause water leakage, therefore it indeed has the necessity to improve.

Please further refer to FIG. 3C, which is a schematic diagram of a conventional water-cup, wherein the conventional water cup 408 is a vacuum-formed cup-body of plastic material. When the cup-body acts, the water is used as a conductive medium to conduct the vibration wave from the outside to the inside. The material of the conventional cup-body is an evenly thick and slightly harder design, often causing the vibration wave to reflect to form the interference phenomenon of disordered waves; which is easy to make the water temperature rise and results in the deformation situation of the cup bottom, this is also the concern of the inventor.

Please refer to FIG. 4A and FIG. 4B, which are respectively the side structure and action schematic diagrams of a conventional nozzle; as can be clearly seen from the figures, the conventional nozzle 10 has an inner screw-thread 10', and an outer screw-thread 20' is set above the gas-gathering unit 20; wherein the metal energy-ring 50 is clamped and combined therebetween in a screw-combining manner, and the smoke generated by the anion essential-oil fragrance machine can be straightly sprayed upward to form a fogging effect; However, when going to bed at night, the user can not directly feel and absorb a large amount of anion smoke, so there is indeed a need for smoke oblique-spray.

SUMMARY OF THE INVENTION

Therefore, the present invention aims to provide an anion essential-oil fragrance machine vibration-wave-conduction cup-bottom-element reinforcement and replaceable water-cup and nozzle structure; in particular, an anion essential-oil fragrance machine has a through hole at the bottom of the vibration-wave-conduction cup; and a component accommodating-chamber and a plurality of radiating rib-bodies are circularly set on the other side of the cup bottom; which the relevant components of the oscillation unit including a silicone ring-sheet and a metal cap-seat can be embedded from bottom to top; then the oscillation unit and a soft pressing-ring are pressurized and set into. Therefore, it can prevent the heat-ablation crack of the bottom of the vibration-wave-conduction cup, which is generated by the long-term action of the high-temperature and high-speed-vibration frequency of the oscillation unit and, it can achieve the main objects to improve the conduction efficiency, prevent leakage, prolong the life of the machine-body components, improve the stability of the machine-body quality, reduce the non-performing rate and the burden of after-sales maintenance man-hours, and save time and effort.

In addition, under the machine-seat, it is set with four foot-hole-slots of the machine-seat which four stopping-slip foot-pads can be embedded into to provide the effects of preventing slip, avoiding vibration, and sound reduction for the machine-body; it is the other object of the present invention.

Further, a soft essential-oil-water cup structure is set in the vibration-wave-conduction cup of the anion essential-oil flagrance machine, which can effectively improve the conduction efficiency, reduce the incidence rate of high temperature, and satisfy the demand of the using habit for using multi essential-oil-water cups; it is another object of the present invention.

Furthermore, the anion essential-oil fragrance machine vibration-wave-conduction cup-bottom-element reinforcement and replaceable water-cup and nozzle structure of the present invention is set with a replaceable nozzle structure between the upside of the gas-gathering unit of the anion essential-oil fragrance machine and the nozzle; which can provide two different types of straight-spray and oblique-spray to satisfy another demand for nighttime sleep; it is another object of the present invention.

DETAILED DESCRIPTION OF THE PREFERRED EMBODIMENTS

Figure 1A:
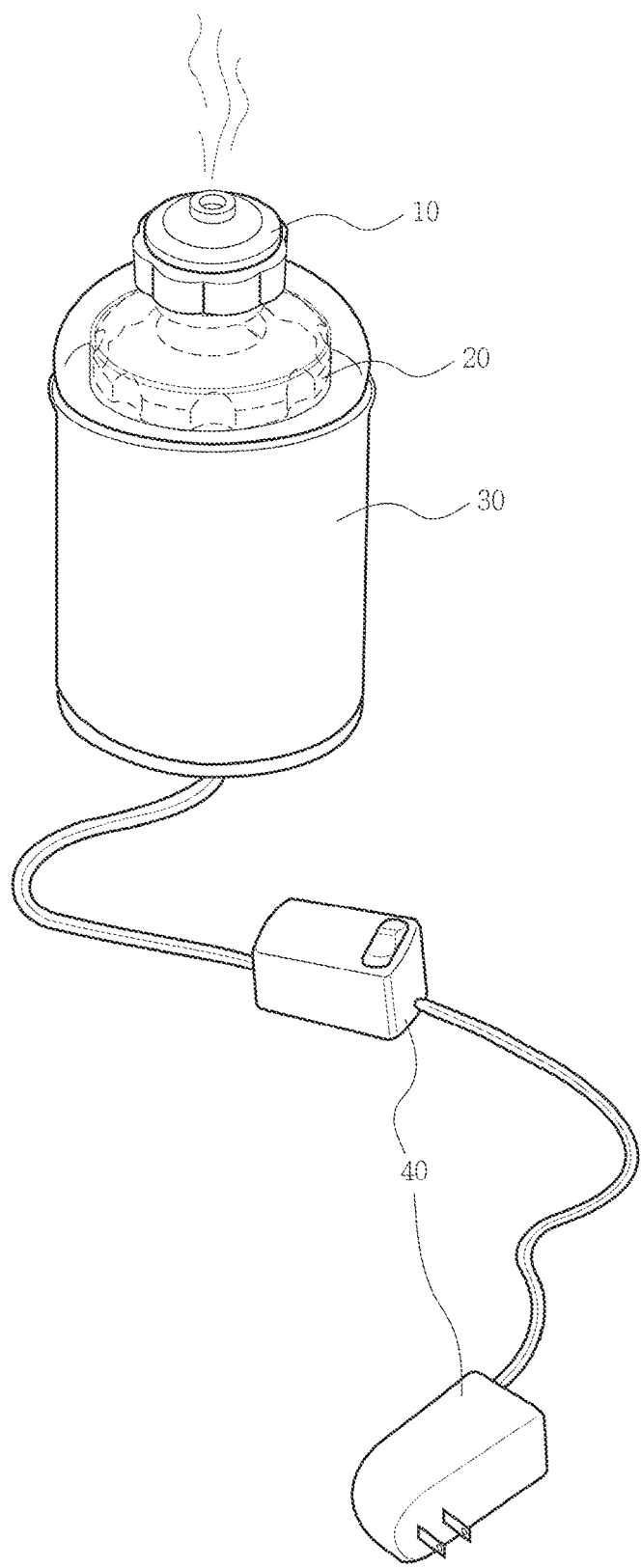
FIG. 1A is a schematic diagram of the appearance of the conventional ultrasonic aroma machine.
Figure 1B:
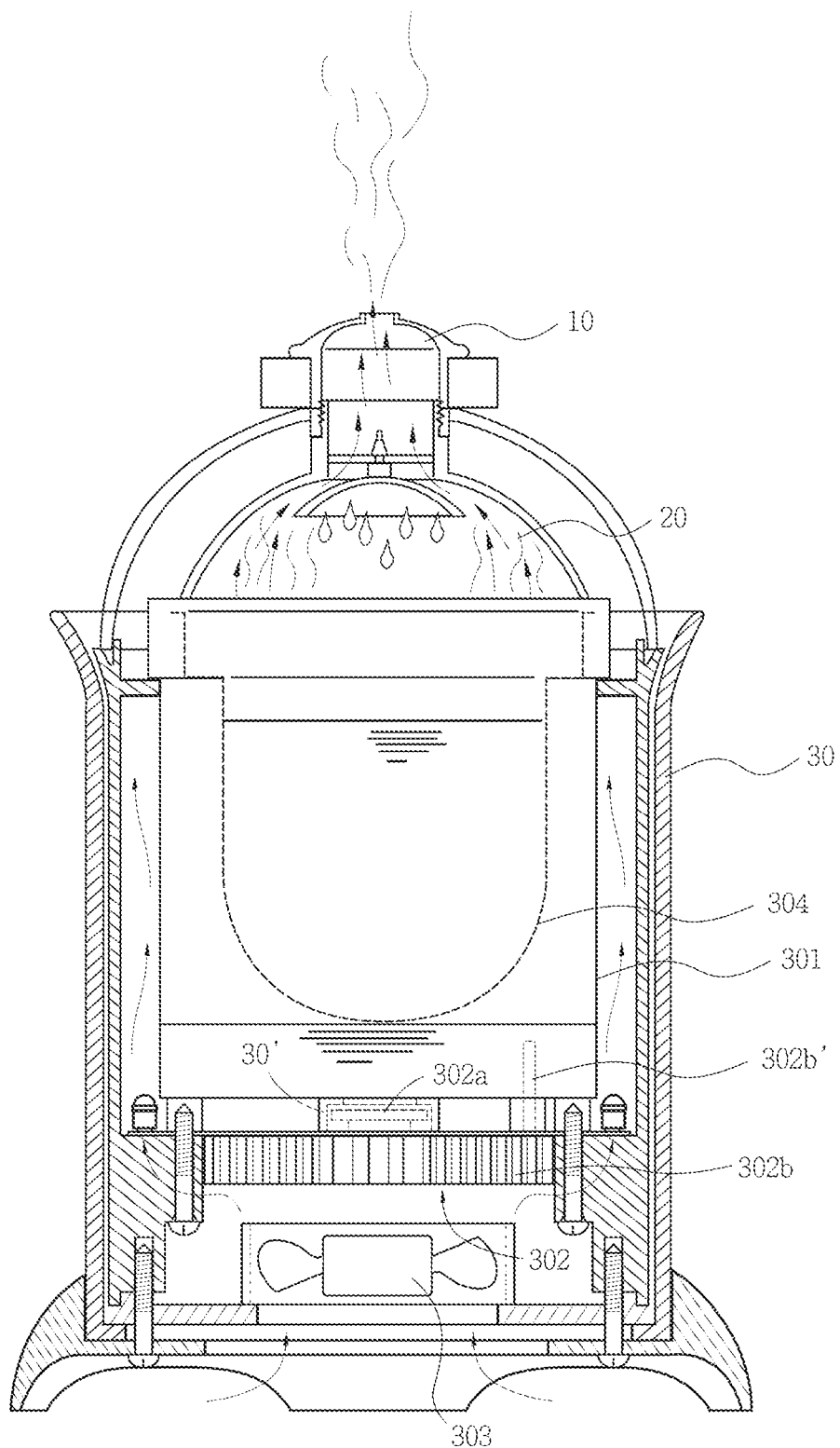
FIG. 1B is a schematic diagram of the side structure of the conventional ultrasonic aroma machine.
Figure 2A:
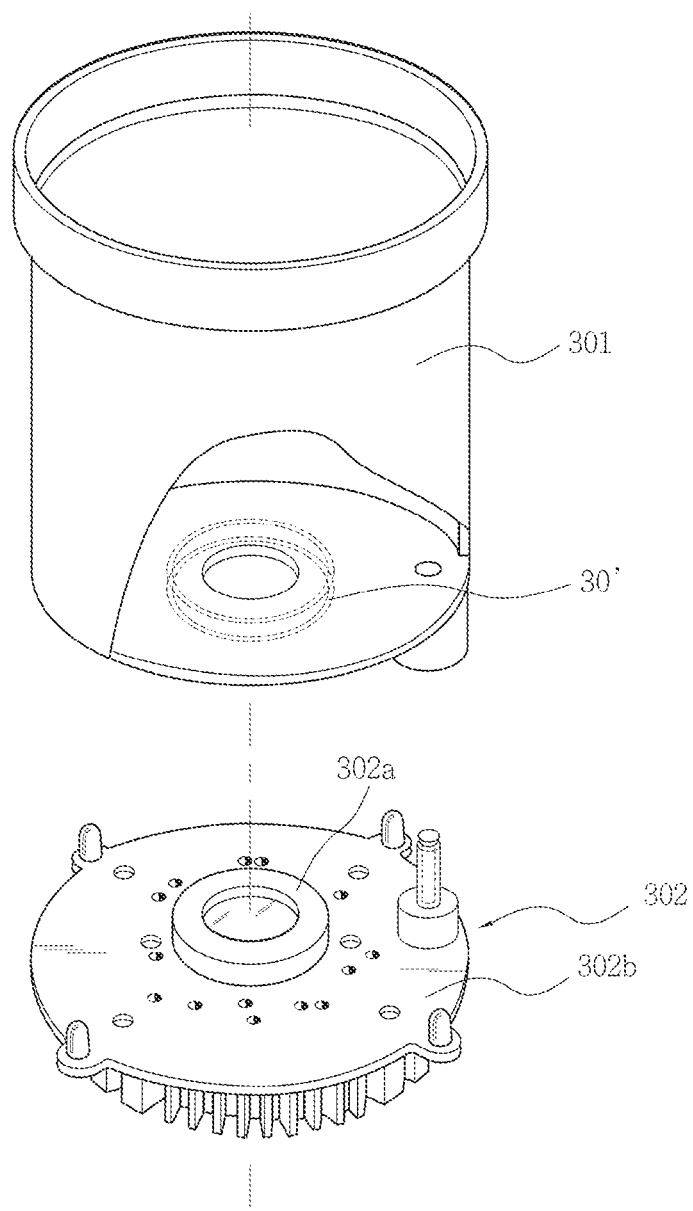
FIG. 2A is an oblique view of a conventional vibration-wave-conduction cup and an oscillation unit.
Figure 2B:
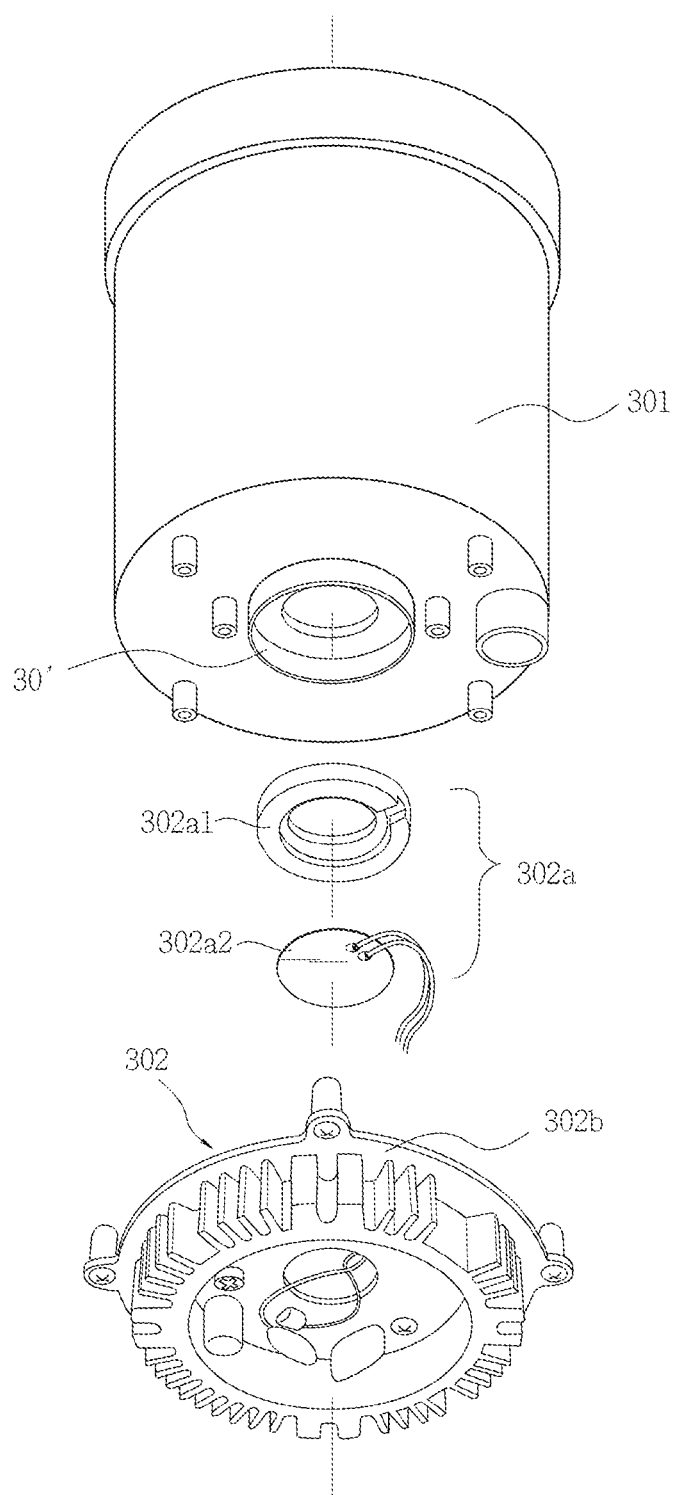
FIG. 2B is a bottom view of a conventional vibration-wave-conduction cup and an oscillation unit.
Figure 2C:
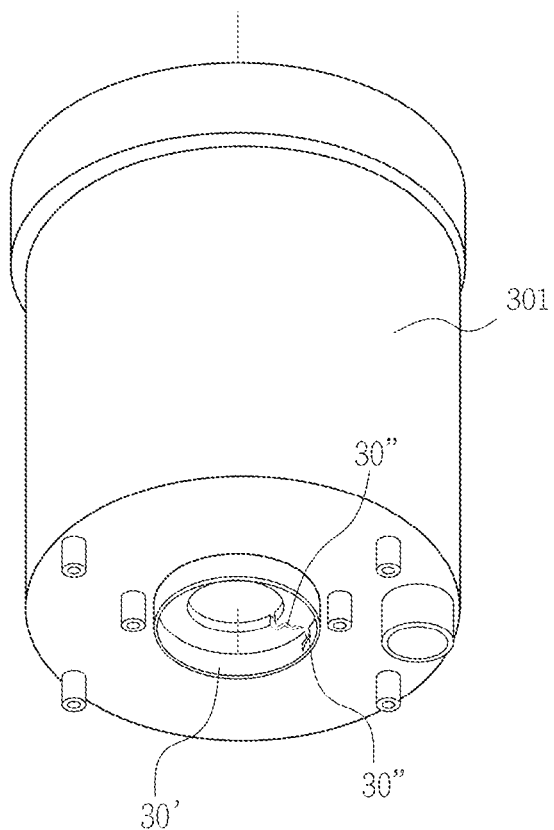
FIG. 2C and FIG. 2D are appearance schematic diagrams of the different angles of view of the conventional vibration-wave-conduction cup at the bottom.
Figure 2D:
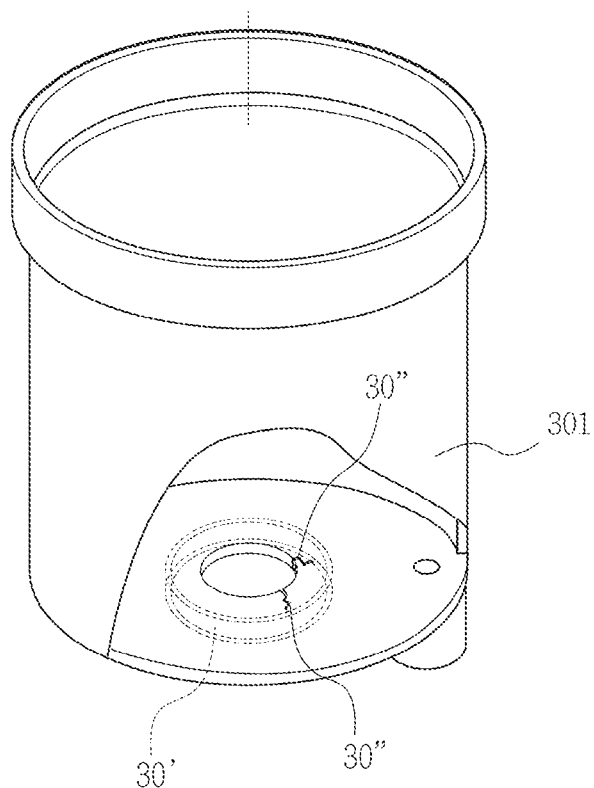
Figure 3A:
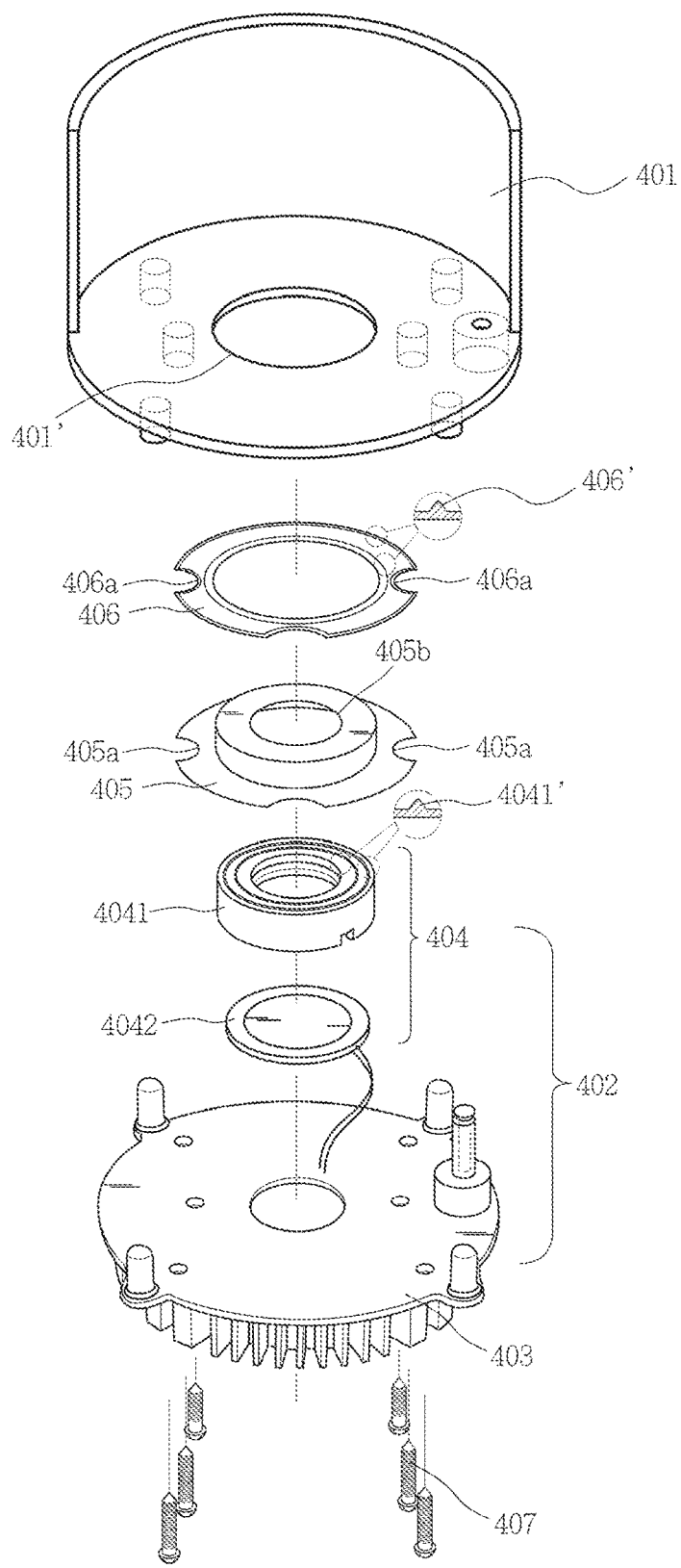
FIG. 3A is a stereoscopic exploded diagram of the previous invention.
Figure 3B:
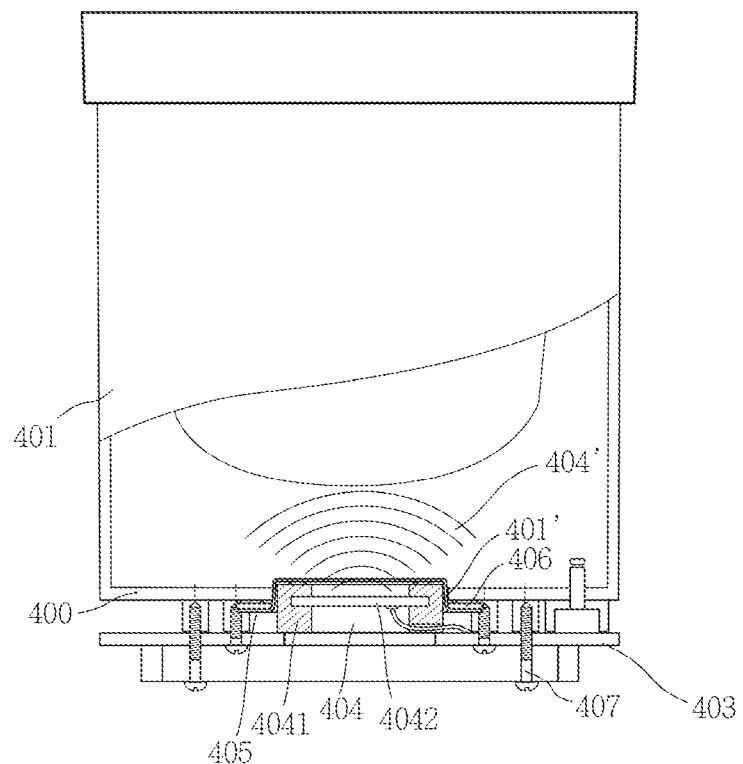
FIG. 3B is a side combination diagram of the previous invention.
Figure 3C:
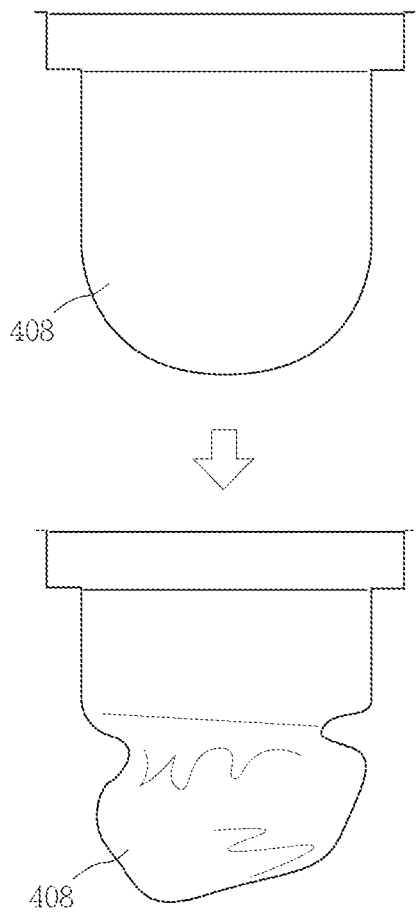
FIG. 3C is a schematic diagram of a conventional water-cup.
Figure 4A:
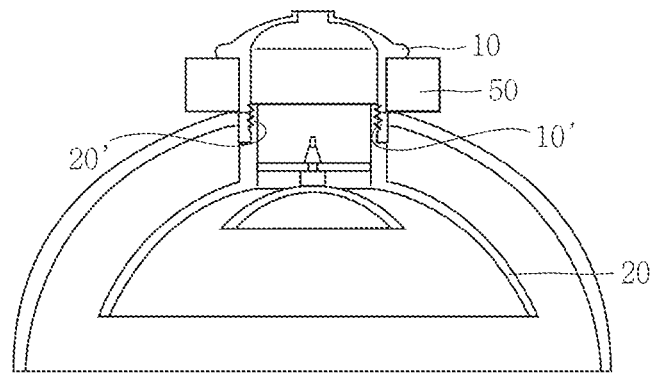
FIG. 4A is a schematic diagram of the side structure of a conventional nozzle.
Figure 4B:
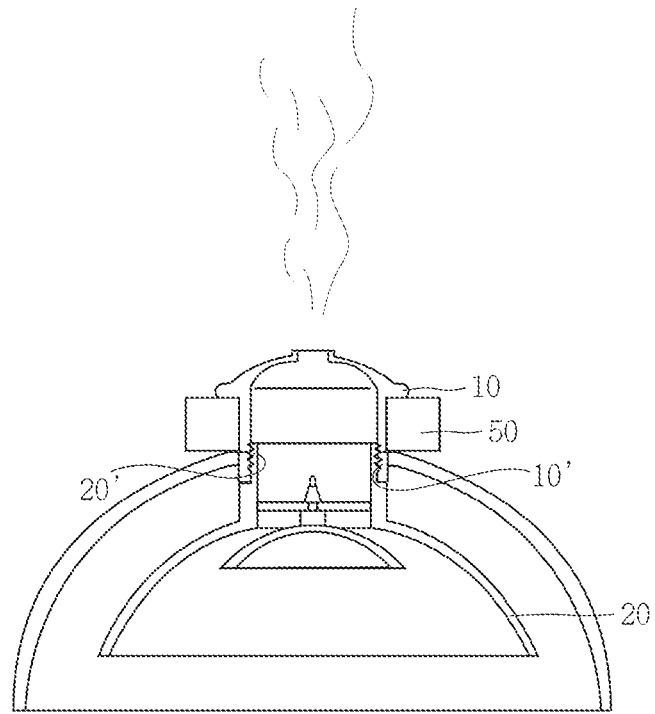
FIG. 4B is an action schematic diagram of a conventional nozzle.
Figure 5:
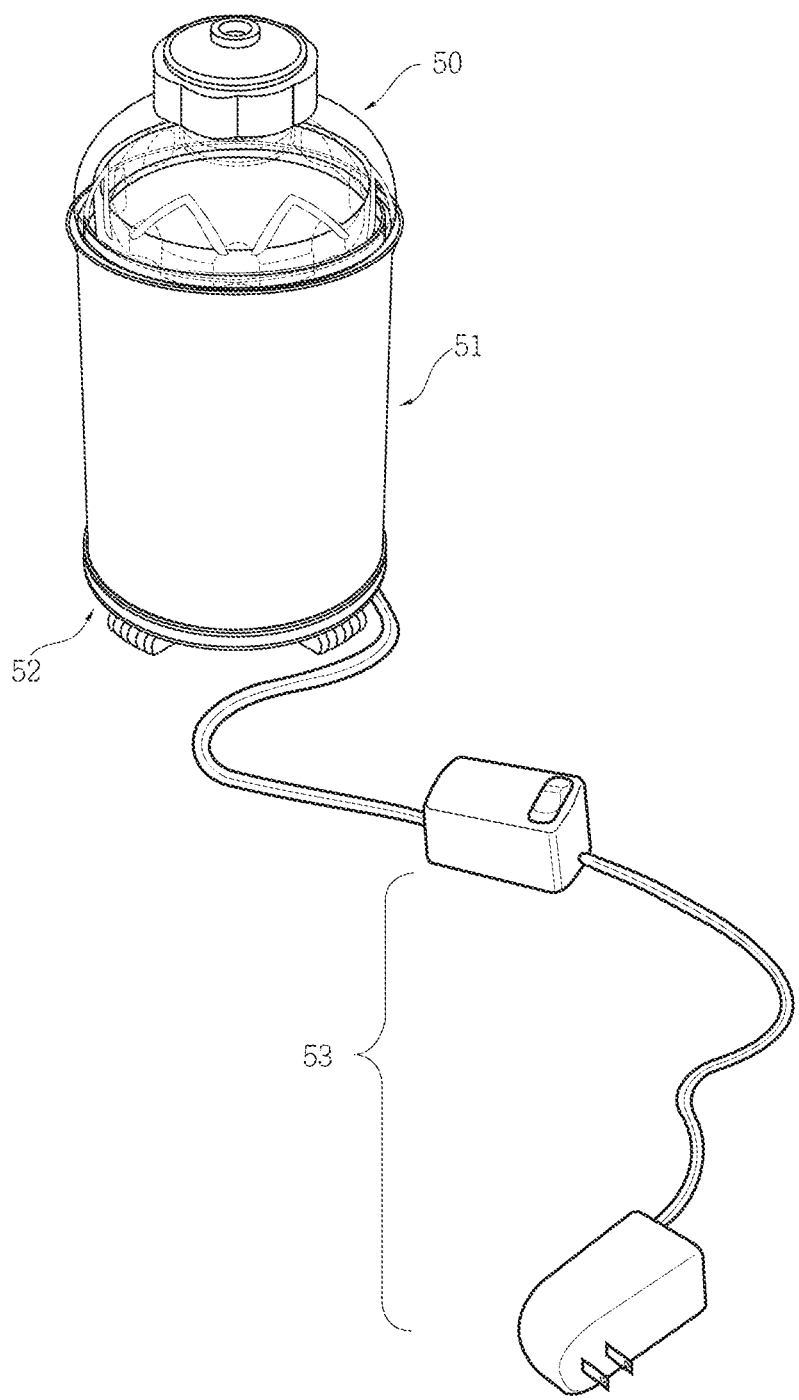
FIG. 5 is a schematic diagram of the appearance of the present invention.
Figure 6A:
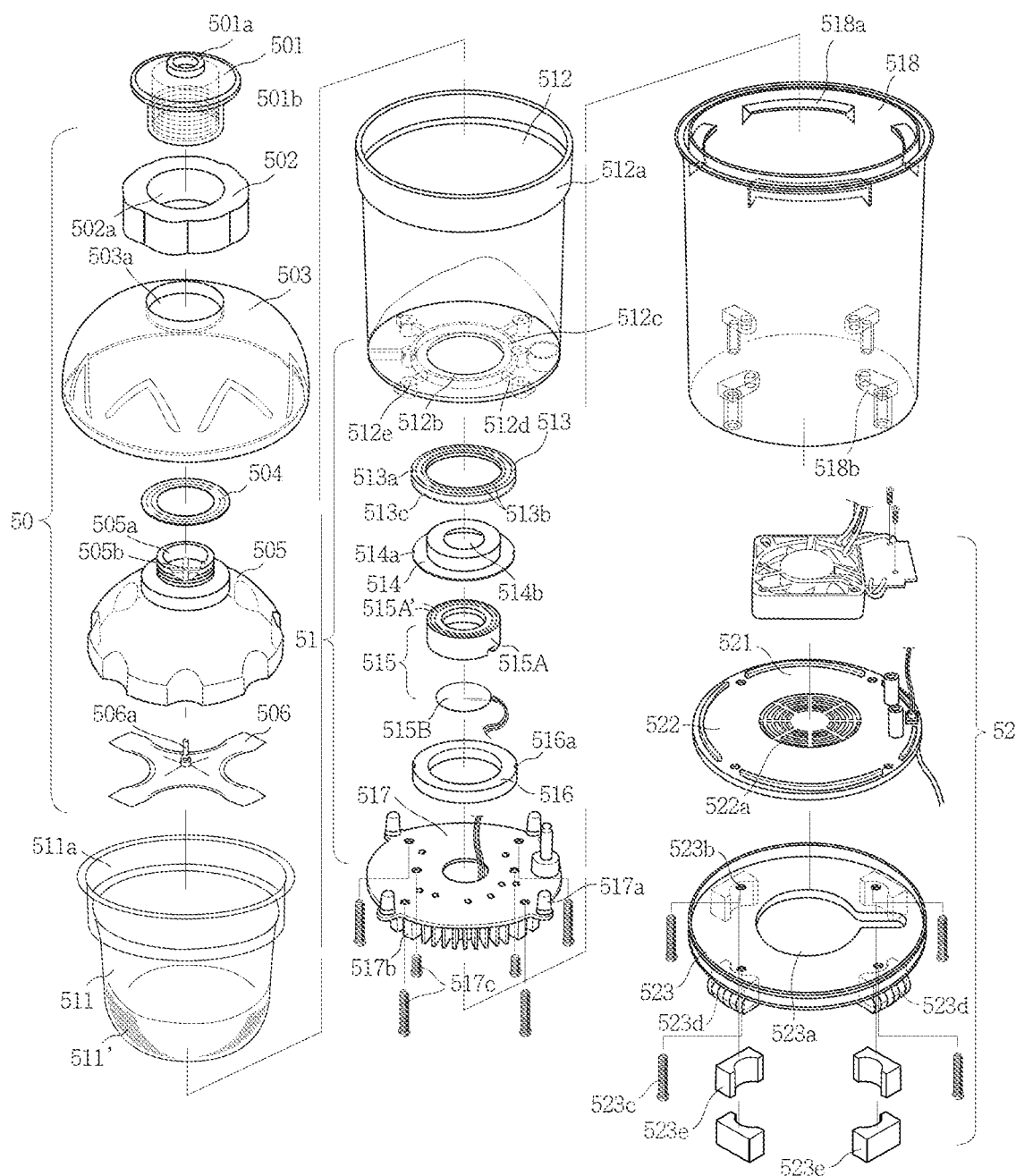
FIG. 6A is a stereoscopic exploded diagram of the present invention.
Figure 6B:
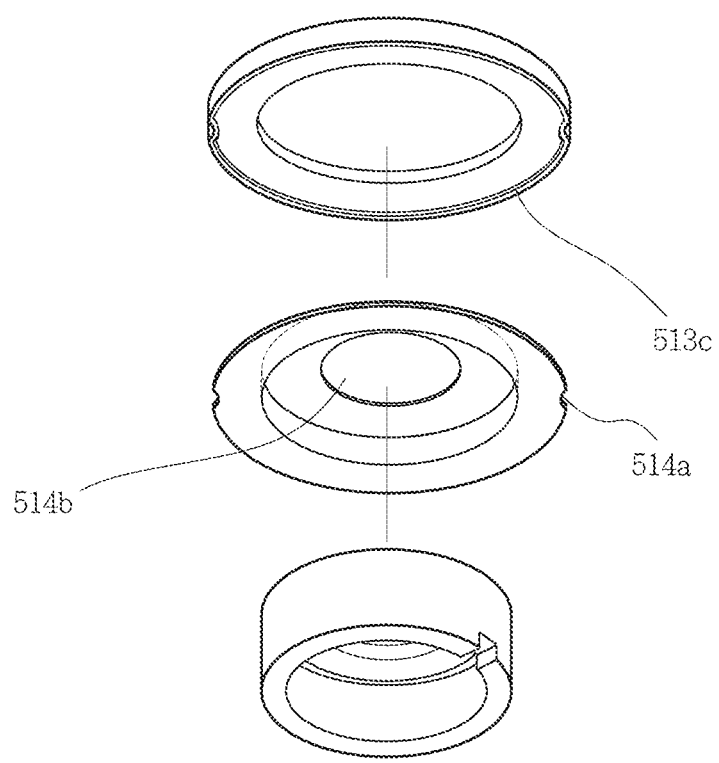
FIG. 6B is a partial structure enlargement diagram of the present invention.
Figure 7:
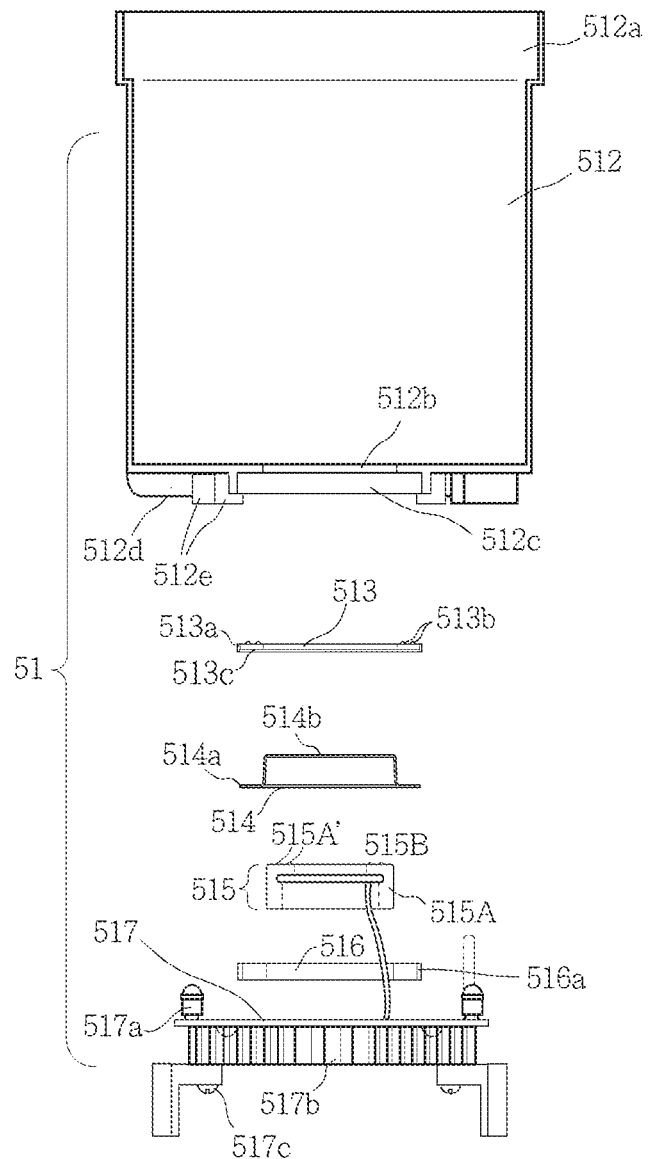
FIG. 7 is a schematic diagram of the side structure of the oscillation unit of the present invention.

The following descriptions are exemplary embodiments only, and are not intended to limit the scope, applicability or configuration of the invention in any way. Rather, the following detailed description provides a convenient illustration for implementing exemplary embodiments of the invention. Various changes to the described embodiments may be made in the function and arrangement of the elements described without departing from the scope of the invention as set forth in the appended claims.

The foregoing and other aspects, features, and utilities of the present invention will be best understood from the following detailed description of the preferred embodiments when read in conjunction with the accompanying drawings.

FIG. 1A to FIG. 4B are related figures of conventional invention, which various defects have been described previously and will not be repeated here.

Please refer to FIG. 5, FIG. 6A, FIG. 6B, and FIG. 7; which are respectively the schematic diagram of the appearance, stereoscopic exploded diagram, partial structure enlargement diagram, and schematic diagram of the side structure of the oscillation unit of the present invention. As can be seen from the figures, the anion essential-oil fragrance machine vibration-wave-conduction cup-bottom-element reinforcement and soft essential-oil-water cup structure of the present invention comprises a gas-gathering unit 50, an oscillation unit 51, an aeration unit 52, and an electronic-control assembly 53; wherein:

The gas-gathering unit 50 comprises a nozzle 501, an energy-ring 502, an upper-hood 503, a ring-seal 504, a gas-gathering hood 505, and a cross blocking-piece 506; wherein the nozzle 501 is a tubular cap-body set with a through hole 501a, and an inner screw-thread 501b is set in the tube; wherein the energy-ring 502 is a magnetic metal ring-body, and a through hole 502a is set in the center; wherein the upper-hood 503 is a semi-spherical hood-body, and a through hole 503a is opened and set in the upper portion; wherein the gas-gathering hood 505 is a conical hood-body, and an outer screw-thread tube-body 505a is set on the top portion; wherein a cross through hole 505b is set in the center of the tube-body, and the lower cross blocking-piece 506 is a soft silicone piece; wherein a barb nail-body 506a is protrudedly set in the center thereof; such that each of the above elements can be screwed, combined, and concatenated with each other into a gas-gathering unit.

And, the oscillation unit 51 comprises a soft water-cup 511, a vibration-wave-conduction cup 512, a silicone ring-sheet 513, a metal cap-seat 514, an oscillation unit 515, a soft pressing-ring 516, a circuit board 517, and an outer cylinder 518; wherein the soft water-cup 511 is a vacuum-formed cup-body of plastic PET material, and the upper part ring-protrudes a wedging-seat 511a; wherein the lower part is a spherical cup type which is softened after being thinned by secondary processing; wherein the upper part of the middle cylinder 512 ring-protrudes a cylinder rim 512a, and a through hole 512b is set at the bottom of the cylinder; wherein a component accommodating-chamber 512c, a plurality of radiating rib-bodies 512d, and a screw-column 512e are ring-set at the near edge of the through hole 512b; wherein the silicone ring-sheet 513 is set with screw-column positioning notches 513a on both sides, and an annular sheet-like body of the inner-outer water-stop-protrusion 513b on the top surface thereof, wherein a ring-protrusion 513c is set on the lower edge of the ring sheet. Please refer to FIG. 6B, which is a partial structure enlargement diagram; wherein the metal cap-seat 514 is a cap-body, which two sides are set with screw-column positioning notches 514a; and a through hole 514b is set on the top surface. And, the oscillation unit 515 is realized by embedding an oscillation element 515B in a silicone seat 515A, wherein a water-stop ring-protrusion 515A' is set above the silicone seat 515A. The soft pressing-ring 516 is a soft silicone ring-body which is set with screw-column positioning notches 516a on both sides. The circuit board 517 is an oscillation circuit substrate, and a plurality of LED lamps 517a are set on the upper side, wherein a heat-sink set 517b and screws 517c are set on the lower side. The outer cylinder 518 is a hollow cylinder-body, the upper inner-edge is convexly set with a positioning ring-piece 518a, and the lower inner-edge is set with four screw-seats 518b.

The aeration unit 52 comprises a fan assembly 521, a bottom-plate 522, and a machine-seat 523; wherein the center of the bottom-plate 522 is set with a ventilation round-grid 522a, and the center of the machine-seat 523 is set with a ventilation hole 523a; wherein a plurality of screw holes 523b are set around the machine-seat 523, and a plurality of combination screws 523c are set under the machine-seat 523; wherein four machine-seat foot-hole-slots 523d which can exactly embed four stopping-slip foot-pads 523e are set below the machine-seat 523. In this way, each of the above elements can be can be screwed, combined, and concatenated with each other into an oscillation unit 51 and an aeration unit 52.

Figure 8:
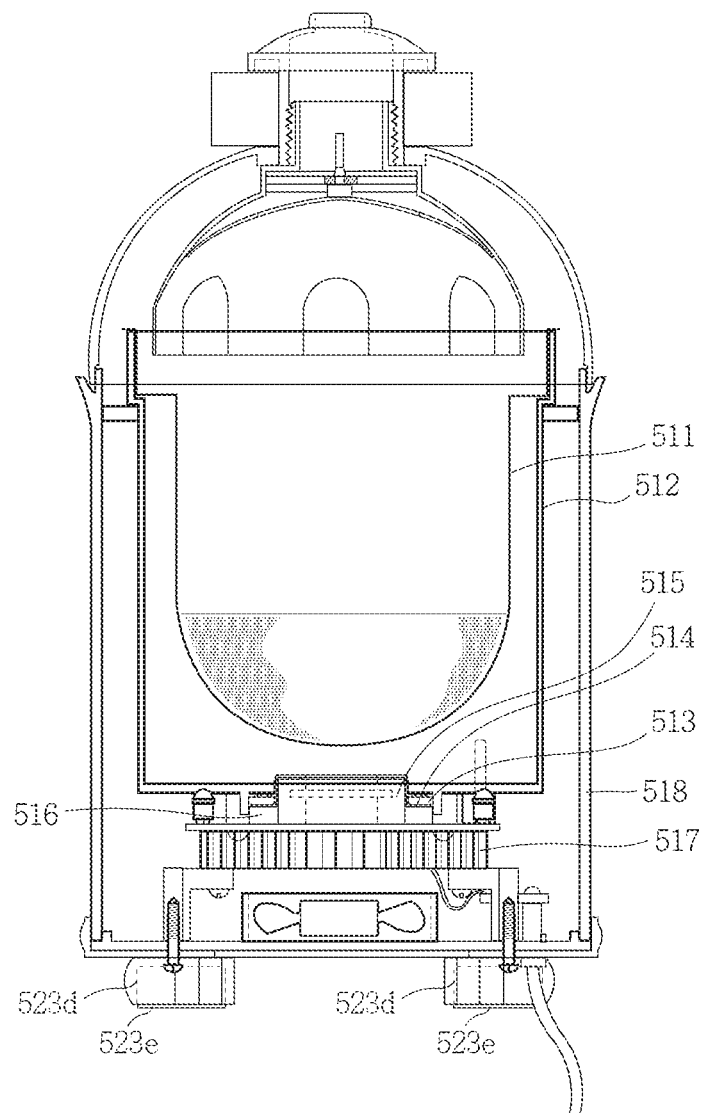
FIG. 8 is a combination diagram of the side structure of the present invention.

Please refer to FIG. 8, which is a combination diagram of the side structure of the present invention; when assembling, the present invention can embed, assemble, screw, and combine the soft water-cup 511, the vibration-wave-conduction cup 512, the silicone ring-sheet 513, the metal cap-seat 514, the oscillation unit 515, the soft pressing-ring 516, the circuit board 517, and the outer cylinder 518; the combination way is extremely precise and the structure has been strengthened, which can greatly improve the performance efficacy and reduce producing the using problem. And, the aeration unit 52 screws and combines the bottom-seat 523, the bottom-plate 522, and the fan assembly 521 into a one-body through a plurality of screws 523c; and which embeds the topping-slip foot-pads 523e to provide the effects of preventing slip, avoiding vibration, and sound reduction for the machine-body.

Figure 9:
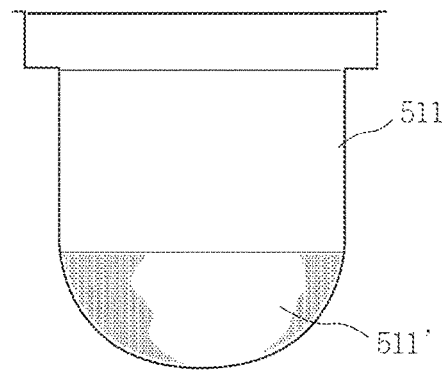
FIG. 9 is a schematic diagram of the soft essential-oil-water cup of the present invention.
Figure 10:
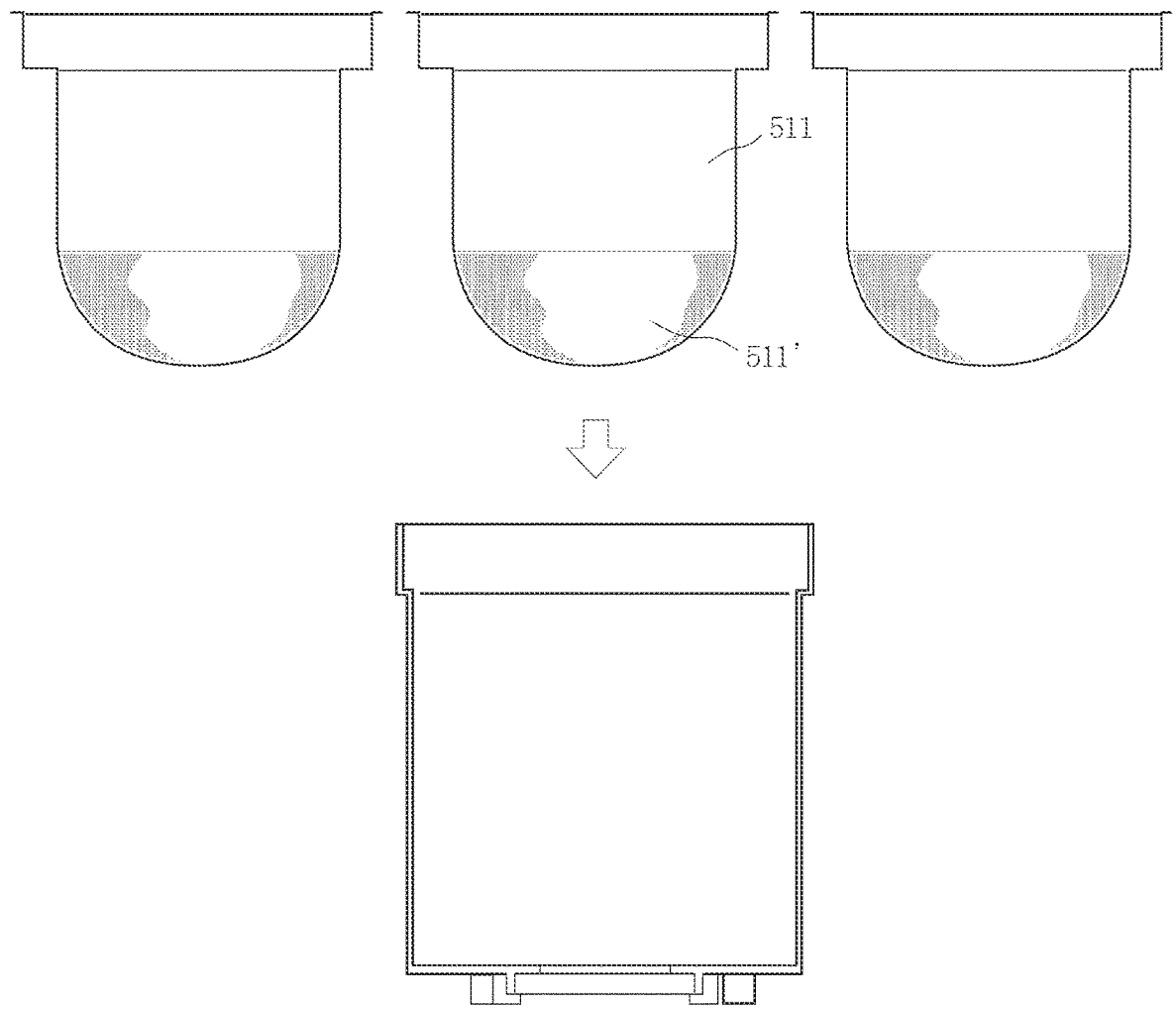
FIG. 10 is a schematic diagram of the replaceable soft essential-oil-water cup of the present invention.

Please refer to FIG. 9 and FIG. 10; which are respectively the schematic diagram of the soft essential-oil-water cup and the schematic diagram of the replaceable soft essential-oil-water cup of the present invention; as can be seen from the figures, the soft water-cup 511 is a vacuum-formed cup-body made of plastic PET material; wherein the lower part is a spherical cup type which is softened after being thinned by secondary processing; by using water as a medium, it is more efficient to provide more effective vibration-wave conduction, and it can also maximally avoid the phenomenon of rising water temperature. In general, the anion essential-oil fragrance machine has the opportunity to use the same water-cup for loading different essential oils, which will cause confusion of the taste; for users with high atmospheric flavor requirement; the characteristic of the replaceable water-cup of the present invention quite satisfies the humanized requirement.

Figure 11A:
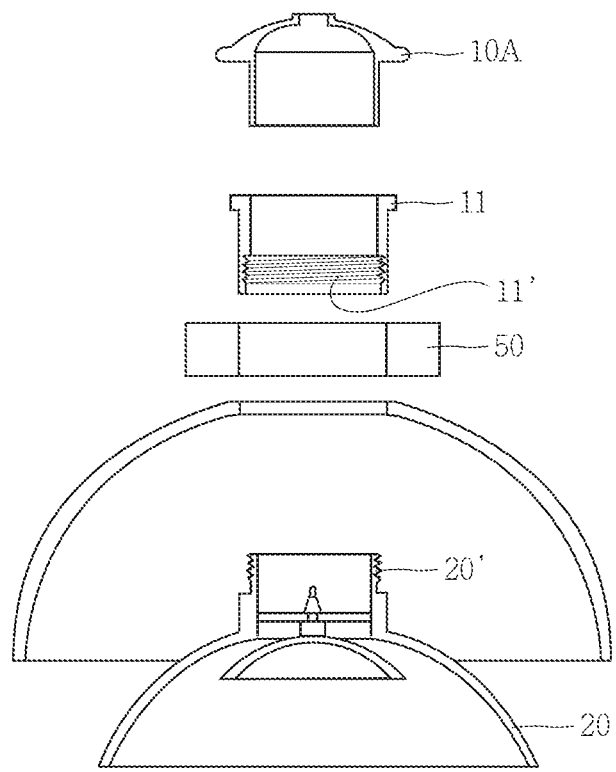
FIG. 11A is a structural exploded diagram of the straight-spray nozzle of the present invention.
Figure 11B:
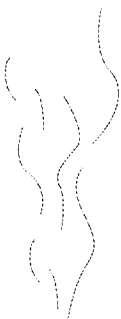
FIG. 11B is a schematic diagram of the straight-spray nozzle of the present invention.
Figure 11B:
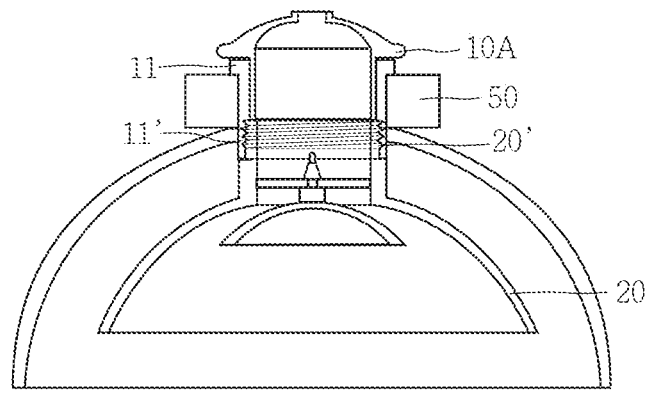

Please refer to FIG. 11A and FIG. 11B; which are respectively the structural exploded diagram of the straight-spray nozzle and the schematic diagram of the straight-spray nozzle of the present invention; as can be seen from the figures, the replaceable nozzle structure of the present invention is set between the upside of the gas-gathering unit 20 and the nozzle 10A, which comprises a straight-spray nozzle 10A and a guiding-connecting barrel-seat 11 having an inner screw-thread 11' underneath, which can be exactly screwed and combined with the outer screw-thread 20' above the gas-gathering unit 20; by sandwiching the metal energy-ring 50 therebetween in a crew-combining manner, the user can select a straight-spray type (such as FIG. 11B) in a larger space or the living room according to the preference.

Figure 12A:
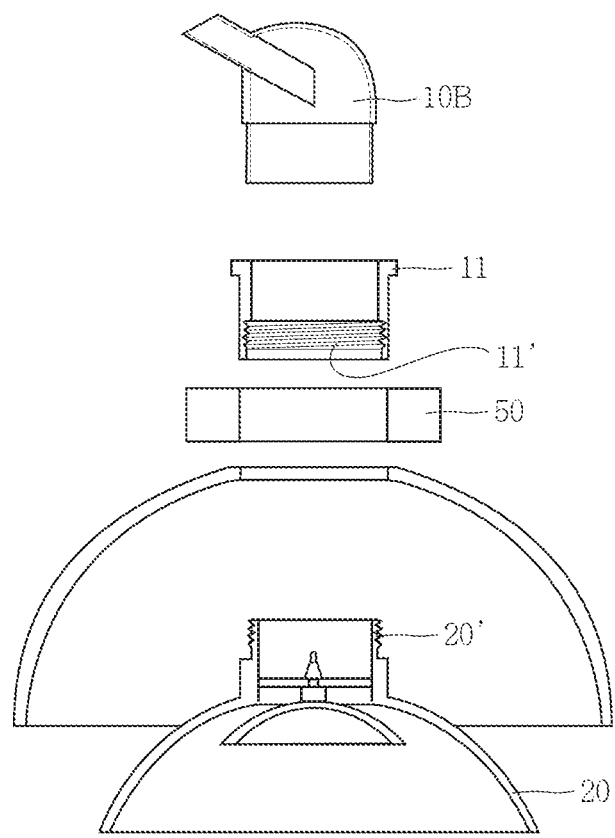
FIG. 12A is a structural exploded diagram of the oblique-spray nozzle of the present invention.
Figure 12B:
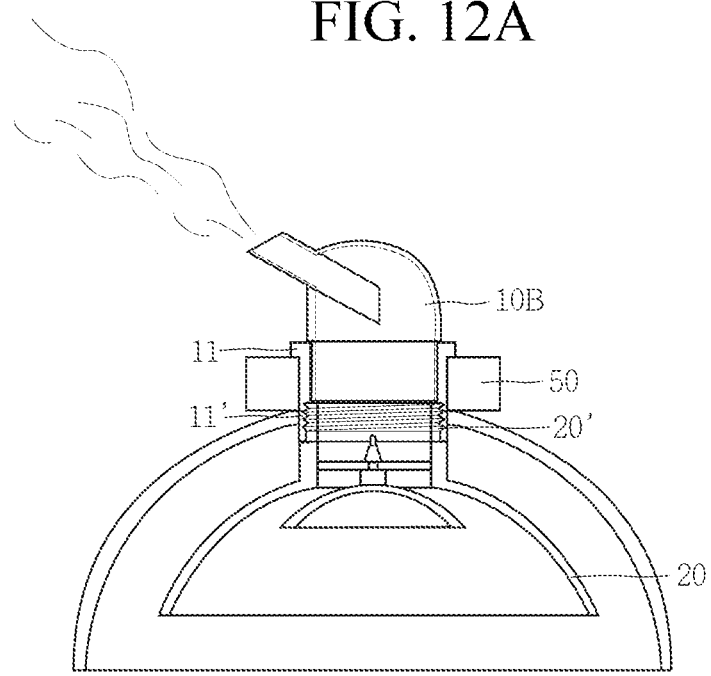
FIG. 12B is a schematic diagram of the other oblique-spray nozzle of the present invention.

Please refer to FIG. 12A and FIG. 12B; which are respectively the structural exploded diagram and the schematic diagram of the oblique-spray nozzle of the present invention; as can be seen from the figures, the replaceable nozzle structure of the present invention is set between the upside of the gas-gathering unit 20 and the nozzle 10B, which comprises an oblique-spray nozzle 10B and a guiding-connecting barrel-seat 11 having an inner screw-thread 11' underneath, which can be exactly screwed and combined with the outer screw-thread 20' above the gas-gathering unit 20; by sandwiching the metal energy-ring 50 therebetween in a crew-combining manner, the user can select an oblique-spray type (such as FIG. 12B) in the bedroom according to the preference; in particular, it helps to directly feel and absorb a large amount of anion smoke when going to bed at night.

I claim:

1. An anion essential-oil fragrance machine comprising: a gas gathering unit, an oscillation unit, an aeration unit, and an electronic control assembly;

wherein the gas gathering unit comprises a nozzle, an energy ring, an upper hood, a ring seal, a gas gathering hood, and a cross blocking piece;

wherein the nozzle is a tubular cap body set with a through hole, and an inner screw-thread is set in a tube;

wherein the energy ring is a magnetic metal ring body, and a through hole is set in a center;

wherein the upper hood is a semi-spherical hood body, and a through hole is opened and set in an upper portion;

wherein the gas gathering hood is a conical hood body, and an outer screw thread tube body is set on a top portion; wherein a cross through hole is set in a center of the tube-body, and a lower cross blocking piece is a soft silicone piece; wherein a barb nail body is protrudedly set in a center thereof;

wherein the oscillation unit comprises a soft water cup, a vibration wave conduction cup, a silicone ring sheet, a metal cap seat, an oscillation unit, a soft pressing ring, a circuit board, and an outer cylinder;

wherein the soft water-cup is a vacuum-formed cup body of plastic PET material, and an upper part ring forms a wedging seat; wherein a lower part is a spherical cup type; wherein an upper part of the vibration wave conduction cup forms a cylinder rim;

wherein a component accommodating chamber, a plurality of radiating rib bodies, and a screw-column are ring-set at a near edge of the through hole;

wherein the silicone ring sheet is set with screw column positioning notches on both sides, and a top surface is set with an annular sheet-like body of an inner-outer water stop protrusion; wherein a ring protrusion is set on a lower edge of the ring sheet;

wherein the metal cap seat is a cap body, which two sides are set with screw column positioning notches; and a through hole is set on a top surface; and, the oscillation unit is realized by embedding an oscillation element in a silicone seat, wherein a water stop ring protrusion is set above the silicone seat;

wherein the soft pressing ring is a soft silicone ring body which is set with screw column positioning notches on both sides;

wherein the circuit board is an oscillation circuit substrate, and a plurality of LED lamps are set on an upper side, and a heat sink set and a plurality screws are set on a lower side;

wherein the outer cylinder is a hollow cylinder-body, an upper inner edge is convexly set with a positioning ring piece, and a lower inner edge is set with four screw seats;

wherein the aeration unit comprises a fan assembly, a bottom plate, and a machine seat; wherein a center of the bottom plate is set with a ventilation round grid, and a center of the machine seat is set with a ventilation hole; wherein a plurality of screw holes are set around the machine seat, and a plurality of combination screws are set under the machine-seat; wherein four machine seat foot hole slots which can exactly embed four stopping slip foot pads are set below the machine-seat.

2. The anion essential-oil fragrance machine according to claim 1, wherein the machine seat foot hole slots are set below the machine seat to receive the stopping slip foot pads, and the stopping slip foot pads are made of soft rubber material to provide the effects of preventing slip, avoiding vibration, and sound reduction for the machine-body.

3. The anion essential-oil fragrance machine according to claim 1, wherein the soft water cup is a vacuum-formed cup body made of plastic PET material, its lower part is a spherical cup type which is softened after being thinned by secondary processing.

4. The anion essential-oil fragrance machine according to claim 1, wherein a replaceable nozzle structure is a structure set between an upside of the gas gathering unit and the nozzle, which comprises a straight-spray nozzle, an oblique-spray nozzle, and a guiding connecting barrel seat, wherein the guiding connecting barrel seat has an inner screw thread underneath, which can be exactly screwed and combined with the outer screw thread above the gas gathering unit.

* * * * *